United States Patent [19]
Knowles

[11] Patent Number: 5,369,158
[45] Date of Patent: Nov. 29, 1994

[54] PHOTOCHROMIC NAPHTHOPYRANS

[75] Inventor: David B. Knowles, Apollo, Pa.

[73] Assignee: Transitions Optical, Inc., Pinellas Park, Fla.

[21] Appl. No.: 71,121

[22] Filed: Jun. 2, 1993

Related U.S. Application Data

[62] Division of Ser. No. 840,378, Feb. 24, 1992, Pat. No. 5,238,981.

[51] Int. Cl.$^5$ .................. C07D 311/92; C07D 333/06; C08K 5/15; C08K 5/34
[52] U.S. Cl. ...................... 524/110; 549/389; 549/331; 549/60; 549/58; 549/32; 546/269; 524/109; 524/99
[58] Field of Search .................... 549/389, 331, 60, 58, 549/32; 546/269; 524/110, 109, 99

[56] References Cited

U.S. PATENT DOCUMENTS

| | | | |
|---|---|---|---|
| 3,562,172 | 1/1972 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 549/389 |
| 4,215,010 | 7/1980 | Hovey et al. | 252/300 |
| 4,342,668 | 8/1982 | Hovey et al. | 252/586 |
| 4,563,458 | 1/1986 | Widdig et al. | 514/253 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,931,221 | 6/1990 | Heller et al. | 252/586 |
| 5,066,818 | 11/1991 | Van Gemert | 549/389 |
| 5,200,116 | 4/1993 | Heller | 252/586 |

FOREIGN PATENT DOCUMENTS

| | | |
|---|---|---|
| 246114 | 5/1987 | European Pat. Off. . |
| 250193 | 6/1987 | European Pat. Off. . |
| 294056 | 12/1988 | European Pat. Off. . |
| 0269471 | 3/1990 | Japan . |

OTHER PUBLICATIONS

Padwa et al, J. Org. Chem., vol. 40, No. 8, 1975.

*Primary Examiner*—Nicky Chan
*Attorney, Agent, or Firm*—Irwin M. Stein

[57] ABSTRACT

Described are novel reversible photochromic naphthopyran compounds substituted at the number eight carbon atom on the naphtho portion of the naphthopyran ring with, for example, a methoxy group. Also described are organic host materials that contain or that are coated with such compounds. Articles such as ophthalmic lenses or other plastic transparencies that incorporate the novel naphthopyran compounds are also described.

16 Claims, No Drawings

PHOTOCHROMIC NAPHTHOPYRANS

This is a division of U.S. application Ser. No. 07/840,378, filed Feb. 24, 1992, now U.S. Pat. No. 5,238,981.

DESCRIPTION OF THE INVENTION

The present invention relates to certain novel naphthopyran compounds. More particularly, this invention relates to novel photochromic naphthopyran compounds with unexpected properties, and to compositions and articles containing such novel naphthopyran compounds. When exposed to light radiation involving ultraviolet (UV) rays, such as the ultraviolet radiation in sunlight or the light of a mercury lamp, many photochromic compounds exhibit a reversible change in color. When the ultraviolet radiation is discontinued, the photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of chromene derivatives, including certain benzopyrans and naphthopyrans. These compounds are described as derivatives of chromene and are reported to undergo a color change, e.g., from colorless to yellow-orange, on irradiation by ultraviolet light at temperatures below about −40° C. Irradiation of the compounds with visible light or upon raising the temperature to within the range of −10° C. to 0° C. is reported to reverse the coloration to a colorless state. U.S. Pat. No. 4,931,221 describes a series of spiropyrans in which two cyclopropyl groups are appended to the position adjacent to the oxygen in the pyran ring. U.S. Pat. No. 4,563,458 describes certain 2H-chromenes as precursors of certain chroman-4-aldehydes, which are reacted with certain amines to prepare 4-aminomethylene-chromans and -chromenes that are used in medicaments.

European Patent Publication 246,114 and U.S. Pat. No. 4,826.977 describe a series of photochromic spiropyrans in which a spiro-adamantane group is appended to the position adjacent to the oxygen in the pyran ring. U.S. Pat. No. 4,818,096 and European Patent Publication 250,193 describe photoreactive plastic lenses that are coated or impregnated with the photochromic spiropyrans of European Patent Publication 246,114 in combination with a photochromic benzopyran or naphthopyran having an aminophenyl substituent at the position adjacent to the oxygen in the pyran ring. European Patent Publication 294,056 describes a process for producing a polyurethane plastic having photochromic properties. Reversible cleavage photochromic compounds disclosed therein include a naphthopyran derivative in which the pyran ring is substituted at the 3-position of the pyran ring with di(p-methoxyphenyl) substituents. Japanese Patent Publication HEI 2(1990)-69471 describes spiropyran compounds in which a norbornylidene group is substituted at the position adjacent to the oxygen in the pyran ring.

Padwa et al in *J. Org. Chem.*, Volume 40, No. 8, 1975, page 1142, describes the investigation of photochemical reactions of 2,2-dimethylbenzopyran and related compounds, identifies the by-products and suggests pathways to the ring-opened color intermediates and the final non-colored phenolics. The color forms examined by the authors are reported as being unstable at room temperature. The authors do not suggest ways in which the stability of the examined compounds might be improved, nor any modification that might be made to the structure of the known pyran compounds.

The present invention relates to novel naphthopyran compounds containing certain substituents at the number eight carbon atom on the naphtho portion of the naphthopyran. The absorption maxima of these compounds have been found to be unexpectedly higher than the corresponding unsubstituted compounds.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes have been of interest because of the potential safety features that such transparencies offer.

Ideal photochromic compounds for use in optical applications, such as conventional ophthalmic lenses, are those which possess (a) a high quantum efficiency for coloring, (b) a relatively fast change in optical density over time, (c) a high optical density at saturation, (d) a low quantum yield for bleaching with visible light and (e) a relatively fast thermal fade at ambient temperature but not so rapid a thermal fade rate that the combination of visible light bleaching and thermal fade prevent coloring by the ultraviolet component of strong sunlight. The aforesaid properties are desirably retained when the photochromic compound is applied to or incorporated within conventional rigid synthetic plastic materials customarily used for ophthalmic and plano lenses. A naphthopyran such as 3,3-diphenyl-3H-naphtho[2,1-b]pyran, changes color on exposure to ultraviolet; but, at room temperature and above, this compound changes optical density too slowly, has too low an optical density at saturation, and bleaches too rapidly for use in an ophthalmic lens.

In accordance with the present invention, there has been discovered certain novel reversible photochromic naphthopyran compounds with unexpected properties. These compounds are substituted at the number eight carbon atom on the naphtho portion of the naphthopyran, and exhibit a dramatic bathochromic shift of their absorption maximum in both the visible spectrum of the activated form and the UV spectrum of the unactivated form. The shift in the UV spectrum has contributed to an increase in sensitivity as measured by how fast the optical density of the compounds change with time, and to an increase in the compounds optical density, as measured by how dark they become, vis a vis, naphthopyrans substituted at the number five, seven or nine carbon atom of the naphtho portion of the naphthopyran. In particular, 3,3-diaryl-3H-naphtho-[2,1-b]pyrans that are appropriately substituted at the number eight carbon atom have a high quantum efficiency for coloring, good sensitivity and saturated optical density, and an acceptable bleach or fade rate. Such compounds are particularly suitable for use in ophthalmic applications.

Naphthopyran compounds contemplated to be within the scope of the present invention may be represented by the following graphic formula I,

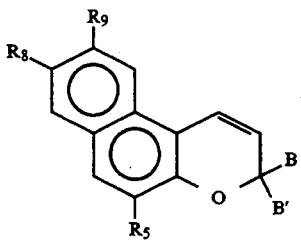

(I)

In graphic formula I, $R_5$ and $R_9$ are each selected from the group consisting of hydrogen, $C_1$–$C_4$ alkoxy, e.g., methoxy, and $C_1$–$C_4$ alkyl, e.g., methyl. $R_8$ is selected from the group consisting of halogen, $C_1$–$C_5$ acyloxy, benzoyloxy, methoxybenzoyloxy, di($C_1$–$C_5$) alkylamino and LO—, wherein L is a $C_1$–$C_{12}$ alkyl, $C_6$–$C_9$ aryl($C_1$–$C_3$)alkyl, $C_5$–$C_7$ cycloalkyl, or $C_1$–$C_4$ alkyl substituted $C_5$–$C_7$ cycloalkyl. The $C_6$–$C_9$ moiety of the $C_6$–$C_9$ aryl($C_1$–$C_3$)alkyl group comprises unsubstituted and alkyl-substituted benzene groups, i.e., mono-, di-, or tri-, alkyl substituted benzene. Preferably, $R_8$ is chloro, bromo, $C_1$–$C_2$ acyloxy, e.g., acetoxy, benzoyloxy, di($C_1$–$C_2$) alkylamino, and LO wherein L is a $C_1$–$C_4$ alkyl, $C_6$–$C_7$ aryl($C_1$–$C_2$)alkyl, $C_5$–$C_6$ cycloalkyl, or $C_1$–$C_2$ alkyl substituted $C_5$–$C_6$ cycloalkyl.

In graphic formula I, B and B' are each selected from the group consisting of (i) the unsubstituted or substituted aryl groups phenyl and naphthyl, (ii) the unsubstituted or substituted heterocyclic aromatic groups pyridyl, thienyl, benzothienyl, furyl and benzofuryl, and (iii) B and B' taken together form the adamantyl group, said aryl and heterocyclic group substituents each being selected from $C_1$–$C_4$ alkyl, $C_1$–$C_4$ haloalkyl, $C_1$–$C_4$ alkoxy, $C_1$–$C_4$ alkoxy($C_1$–$C_4$)alkyl, di($C_1$–$C_5$)alkylamino and halogen, said halogen (halo) substituents being selected from fluorine, chlorine and bromine, provided that at least one of B and B' is a substituted or unsubstituted phenyl group except when B and B' form the adamantyl group.

Preferably B and B' are each phenyl or substituted phenyl, e.g., mono- or di-($C_1$–$C_4$)alkyl substituted phenyl, such as methylphenyl; mono- or di-($C_1$–$C_4$)alkoxy substituted phenyl, such as methoxyphenyl; and halophenyl, such as chlorophenyl and fluorophenyl. The phenyl substituents may be located at the ortho, meta, and/or para positions. Typically, the substituted phenyl contains less than 3 substituents, i.e., zero (none), one or two substituents. More particularly, B and B' are the substituted phenyl groups represented by the following graphic formulae I-A and I-B respectively,

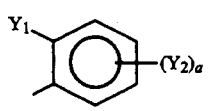

(I-A)

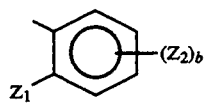

(I-B)

wherein $Y_1$ may be selected from the group consisting of $C_1$–$C_5$ alkyl, e.g., methyl, ethyl, propyl, butyl and pentyl, $C_1$–$C_5$ alkoxy, e.g., methoxy, ethoxy, propoxy, butoxy and pentoxy, fluoro and chloro, preferably $C_1$–$C_3$ alkyl, $C_1$–$C_3$ alkoxy and fluoro; $Z_1$ may be selected from the group consisting of hydrogen and $Y_1$, preferably hydrogen; each $Y_2$ and $Z_2$ may be selected from the group consisting of $C_1$–$C_5$ alkyl, $C_1$–$C_5$ alkoxy, cyano, hydroxy, halogen, preferably chloro or fluoro, acrylyl, methacrylyl, acryloxy ($C_1$–$C_4$) alkyl, and methacryloxy ($C_1$–$C_4$) alkyl. Preferably, each $Y_2$ and $Z_2$ are selected from the group consisting of $C_1$–$C_3$ alkyl, $C_1$–$C_3$ alkoxy and fluoro. In a particular embodiment, $Y_2$ is $C_1$–$C_3$ alkyl or $C_1$–$C_3$ alkoxy, $Z_2$ is $C_1$–$C_3$ alkyl, or $C_1$–$C_3$ alkoxy; and a and b are each integers of from 0 to 2; preferably a is 0 or 1, and b is 0, 1 or 2. The positioning of the $Y_2$ and $Z_2$ substituents is preferably in the 3,4 or 5 positions. When a or b is 1, the preferred position is meta or para to the carbon atom attached to the pyran ring. When a or b is 2, the positions are preferably at the 3 and 4, 3 and 5, or 4 and 5 numbered carbon atoms.

Compounds represented by graphic formulae I may be prepared by various synthetic routes. For example, the reaction of 2,6-dihydroxynaphthalene with an appropriate reagent, e.g, dimethyl sulfate will yield the corresponding substituted hydroxynaphthalene e.g., 6-methoxy-2-hydroxynaphthalene. The intermediate 6-substituted-2-hydroxynaphthalene may then be reacted further with the appropriate disubstituted, i.e., B,B'-substituted, propargyl alcohol, e.g., 1,1-diphenyl-2-propyn-1-ol, under acidic conditions to form compounds of graphic formula I. Because of the limited availability of 2,6-dihydroxynaphthalene, it is contemplated that other substituted dihydroxynaphthalene starting reagents, i.e, 2,3-dihydroxynaphthalene-6-sulfonic acid sodium salt and 2,7-dihydroxynaphthalene-3-6-disulfonic acid disodium salts, which are more readily available in commercial quantities, may be used to synthesize the compounds of graphic formula I. The presence of an alkoxy group, e.g., methoxy, on the number 5 and/or 9 carbon atoms of the resulting naphthopyran compound does not affect the unexpected photochromic properties observed for the naphthopyran compounds having the described substituents on the number 8 carbon atom. It is also contemplated that other starting dihydroxynaphthalene reagents which result in substituents on the naphtho portion of the naphthopyran (in addition to the desired substituent on the number 8 carbon atom) that do not affect the observed unexpected bathochromic shift of the absorption maximum may be used to synthesize the naphthopyran compounds of graphic formula I.

Compounds represented by graphic formula I may be used in those applications in which organic photochromic substances may be employed, such as for example in optical lenses, e.g., ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., in coating compositions such as paints. Naphthopyrans represented by graphic formula I exhibit color changes from colorless to colors ranging from yellow to orange.

Of particular current interest are the following naphthopyrans:

(1) 8-methoxy-3,3-diphenyl-3H-naphtho [2,1-b]pyran.

(2) 8-methoxy-3-(2-fluorophenyl)-3-(4-methoxyphenyl)-3H-naphtho[2,1-b]pyran.

(3) 8-methoxy-3-phenyl-3-(4-methylphenyl)-3H-naphtho[2,1-b]pyran.

(4) 8-methoxy-3-phenyl-3-(4-trifluoromethylphenyl)-3H-naphtho[2,1-b]pyran.

(5) 8-methoxy-3-(2-fluorophenyl)-3-(4-methylphenyl)-3H-naphtho[2,1-b]pyran (6) 8-methoxy-3-(4-dimethylaminophenyl)-3-(phenyl)-3H-naphtho[2,1-b]pyran.

(7) 5,8-dimethoxy-3,3-diphenyl-3H-naphtho[2,1-b]pyran.

(8) 8-bromo-3-phenyl-3-(4-methylphenyl)-3H-naphtho[2,1-b]pyran.

(9) 5,8,9-trimethoxy-3,3-diphenyl-3H-naphtho[2,1-b]pyran.

Naphthopyrans described herein may be dissolved in common organic solvents such as benzene, toluene, chloroform, ethyl acetate, methyl ethyl ketone, acetone, ethyl alcohol, methyl alcohol, acetonitrile, tetrahydrofuran, dioxane, methyl ether of ethylene glycol, dimethylformamide, dimethylsulfoxide, morpholine and ethylene glycol. They may also be dispersed in fluorocarbons and in liquids containing water and/or alcohols.

The aforedescribed naphthopyran compounds may also be dissolved in solutions prepared with transparent organic host materials, e.g., transparent polymers (homopolymers or copolymers) or blends of such transparent polymers and optionally a suitable organic solvent, e.g., transparent polymers dissolved in one or more of the aforedescribed organic solvents. Examples of such solutions include a poly(vinyl acetate)-acetone solution, a nitrocellulose-acetonitrile solution, a poly(vinyl chloride)-methyl ethyl ketone solution, a poly(methylmethacrylate)-acetone solution, a cellulose acetate-dimethylformamide solution, a poly(vinyl pyrrolidone)acetonitrile solution, a polystyrene-benzene solution and an ethyl cellulose-methylene chloride solution. The aforesaid photochromic solutions or compositions may be applied to a compatible host material, e.g., a transparent support, such as cellulose triacetate, polyethylene terephthalate or baryta paper and dried to obtain an article that will color on exposure to ultraviolet radiation and that will return to its original state by removing the source of ultraviolet radiation.

The naphthopyran compounds described herein (or compositions containing them) may be applied to or incorporated also within a coating composition applied to a compatible support; or applied to or incorporated within the article comprising the compatible host, e.g., a polymerized organic material such as a synthetic polymeric plastic host material.

The naphthopyrans described hereinabove may be incorporated in synthetic plastic materials customarily used for plastic optical lenses, both plano and ophthalmic, e.g., materials such as methyl methacrylate, polycarbonates and polymerizates prepared from CR-3 ® diallyl glycol carbonate monomer.

On irradiation of the compounds of graphic formula I with ultraviolet light, the naphthopyran ring is believed to open reversibly at the carbon-oxygen bond between the number 3-carbon atom and the ring oxygen. The formation of the open form of the colorless compound is believed to be responsible for the coloring observed on exposure to ultraviolet light. The colored form of the photochromic compounds of graphic formula I will fade to the colorless state at normal ambient temperatures when not exposed to ultraviolet light.

Commercially available photoreactive inorganic glass ophthalmic lenses containing silver halide particles darken to a gray or brown color in sunlight. In order to duplicate this color change in a plastic lens using the organic photochromic naphthopyrans of graphic formula I, it is contemplated that such naphthopyrans be used in combination with other appropriate complementary organic photochromic materials so that together they produce the desired near neutral gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

Spiro(indolino) pyrido benzoxazine photochromic compounds described in U.S. Pat. No. 4,637,698 and spiro(indolino) naphthoxazines described in U.S. Pat. Nos. 3,562,172, 3,578,602, 4,215,010 and 4,342,668 are reported to color to colors ranging from purple to blue when activated, and these compounds may be used in admixture with or in conjunction with the yellow-orange novel naphthopyran photochromic compounds described in this application to obtain a near gray color when exposed to unfiltered sunlight. In addition, certain spiro(indolino)benzoxazines described in U.S. Pat. No. 4,816,584 color to shades of purple/blue when activated, and these compounds may be used also in admixture with or in conjunction with the photochromic naphthopyrans described in this application.

The aforesaid first mentioned spiro(indolino)-type compounds may be represented by the following graphic formula:

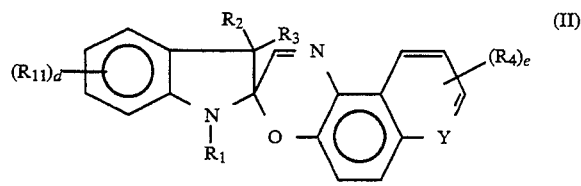

In the above graphic formula II, $R_1$ may be selected from the group consisting of $C_1$-$C_8$ alkyl, e.g., methyl, ethyl, n-propyl, isopropyl, butyl, etc., phenyl, phen(-$C_1$-$C_4$)alkyl, e.g., benzyl, naphth($C_1$-$C_4$)alkyl, e.g., 1-naphthylmethyl, allyl, acrylyl($C_2$-$C_6$)alkyl, methacrylyl-($C_2$-$C_6$)alkyl, carboxy($C_2$-$C_6$)alkyl, e.g., β-carboxyethyl, γ-carboxypropyl, δ-carboxybutyl, cyano($C_2$-$C_6$)alkyl, e.g., β-cyanoethyl, γ-cyanopropyl, β-cyanoisopropyl, and δ-cyanobutyl, $C_1$-$C_4$ acyloxy($C_2$-$C_6$)alkyl, i.e., [$R_cC(O)OR_d$—, wherein $R_c$ is a $C_1$-$C_4$ alkyl and $R_d$ is a $C_2$-$C_6$ alkyl], e.g., acetoxyethyl, acetoxypropyl, propionyloxyethyl, acetoxybutyl, and propionyloxypropyl, hydroxy($C_2$-$C_6$)alkyl, e.g., hydroxyethyl, hydroxypropyl and hydroxybutyl, $(C_2H_4O)_m$·$CH_3$, wherein m is a number of from 1 to 6, and mono- and disubstituted phenyl, said phenyl substituents being selected from $C_1$-$C_4$ alkyl and $C_1$-$C_5$ alkoxy, e.g., methoxy, ethoxy, propoxy, butoxy and pentoxy. Preferably, $R_1$ is selected from the group consisting of $C_1$-$C_4$ alkyl, phenyl, benzyl, 1-naphth($C_1$-$C_2$)alkyl, such as 1-naphthylmethyl, carboxy($C_2$-$C_4$)alkyl, cyano($C_2$-$C_4$)alkyl, $C_1$-$C_4$ acyloxy($C_2$-$C_4$)alkyl, e.g., $C_1$-$C_4$ acyloxyethyl, hydroxy($C_2$-$C_4$)alkyl, and $(C_2H_4O)_m$·$CH_3$, wherein m is a number of from 1 to 3, e.g., 2.

$R_2$ and $R_3$ of the above graphic formula II may each be selected from the group consisting of $C_1$-$C_5$ alkyl, phenyl, mono- and disubstituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1$-$C_4$ alkyl and $C_1$-$C_5$ alkoxy radicals. More particularly, $R_2$ and $R_3$ are each selected from $C_1$-$C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

Y in graphic formula II may be carbon or nitrogen. The number and type of non-hydrogen substituent groups represented by $R_4$ will vary depending upon whether Y is carbon or nitrogen. Generally, when Y is carbon each $R_4$ substituent may be selected from the group consisting of halogen, e.g., chloro, fluoro, or bromo, $C_1$-$C_5$ alkyl, $C_1$-$C_5$ alkoxy, e.g., methoxy, ethoxy, propoxy, butoxy and pentoxy, nitro, cyano, thiocyano, $C_1$-$C_4$ monohaloalkyl, e.g., $C_1$-$C_4$ monochloroalkyl, such as chloromethyl and chloroethyl, $C_1$-$C_2$ polyhaloalkyl, as, for example, trihaloalkyl such as trichloroalkyl or trifluoroalkyl, e.g., trifluoromethyl and 2,2,2-trifluoroethyl, and monoalkylamino or dialkylamino wherein the alkyl moiety of the alkylamino group contains from one to four carbon atoms, e.g., methylamino, ethylamino, propylamino, dtmethylamino and diethylamino.

The letter "e" in graphic formula II is an integer of from 0 to 2, e.g., 1, and denotes the number of non-hydrogen $R_4$ substituents. In particular, when "e" is 1 or 2 and Y is carbon, each $R_4$ substituent may be selected from the group $C_1$-$C_2$ alkyl, $C_1$-$C_2$ alkoxy, chloro, fluoro, bromo, nitro, and trifluoromethyl. When "e" is 0 (zero), there are no $R_4$ substituents and all of the aromatic carbon atoms in the naphtho group have their full complement of hydrogen atoms for the aromatic group shown.

When Y is nitrogen, each $R_4$ (non-hydrogen) substituent may be selected from $C_1$-$C_5$ alkyl, e.g., $C_1$-$C_2$ alkyl, $C_1$-$C_5$ alkoxy, e.g., $C_1$-$C_2$ alkoxy, and halogen, e.g., chloro, fluoro or bromo. Typically, "e" is 0 (zero) when Y is nitrogen and thus there are no $R_4$ substituents.

Each $R_{11}$ in graphic formula II may be selected from $C_1$-$C_5$ alkyl, halogen, $C_1$-$C_5$ alkoxy, nitro, cyano, $C_1$-$C_4$ monohaloalkyl, $C_1$-$C_4$ polyhaloalkyl, $C_1$-$C_8$ alkoxycarbonyl, and $C_1$-$C_4$ acyloxy, i.e., $R_cC(O)O$—, wherein $R_c$ is a $C_1$-$C_4$ alkyl, e.g., methyl. The letter "d" in graphic formula II represents an integer that may vary from 0 to 4, e.g., 0 to 2, such as 1 or 2, and denotes the number of non-hydrogen substituents. When "d" is 0 (zero), there are no $R_{11}$ substituents and all of the aromatic carbon atoms have their full complement of hydrogen atoms for the indole group.

More particularly, spiro(indolino) pyridobenzoxazines (when Y is nitrogen) may be represented by the following graphic formula:

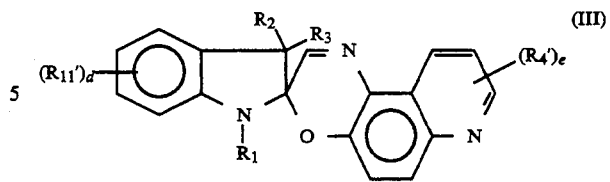

In graphic formula III, $R_1$, $R_2$ and $R_3$ are the same as defined with respect to graphic formula II. Each $R_4'$ may be selected from $C_1$-$C_5$ alkyl, e.g., $C_1$-$C_2$ alkyl, $C_1$-$C_5$ alkoxy, e.g., $C_1$-$C_2$ alkoxy and halogen, e.g., chloro, fluoro or bromo. The letter "e" may be 0 or 1. Commonly, "e" is 0, and thus, there are no $R_4'$ substituents. When "e" is 1, the $R_4$ substituent may be located on any of the available carbon atoms of the pyrido moiety of the pyrido benzoxazine portion of the compound, i.e., at the 5', 6', 8' 9' or 10' positions, most usually at the 8', 9' or 10' positions.

Each $R_{11}'$ in graphic formula III may be selected from the group consisting of $C_1$-$C_5$ alkyl, e.g., methyl, ethyl, propyl, butyl and pentyl, halogen, e.g., chloro and fluoro, $C_1$-$C_5$ alkoxy, e.g., methoxy, ethoxy, propoxy, butoxy and pentoxy, nitro, cyano, $C_1$-$C_4$ monohaloalkyl, e.g., chloromethyl, fluoromethyl, chloroethyl, chloropropyl, etc., $C_1$-$C_4$ polyhaloalkyl, e.g., trihaloalkyl, $C_1$-$C_8$ alkoxycarbonyl, and $C_1$-$C_4$ acyloxy, i.e., $R_cC(O)O$—, wherein $R_c$ is a $C_1$-$C_4$ alkyl, e.g., methyl. An example of an acyloxy group is acetoxy. While any halogen, i.e., chlorine, bromine, iodine and fluorine may be used in respect to the aforesaid halogen or haloalkyl substituents, chlorine, fluorine and bromine, particularly chlorine and fluorine, are preferred for the halogen substituent and fluorine is preferred for the polyhaloalkyl substituent, e.g., trifluoromethyl, ($CF_3$). Preferably, $R_{11}'$ is selected from the group consisting of $C_1$-$C_2$ alkyl, chlorine, fluorine, $C_1$-$C_2$ trihaloalkyl, e.g., trihalomethyl such as trifluoromethyl and $C_1$-$C_5$ alkoxy.

The letter "d" in graphic formula III is an integer from 0 to 4, e.g., 0 to 2, such as 1 or 2. When "d" is 2 or more, each $R_{11}'$ substituent may be the same or different and in either case, are selected from the aforedescribed group. The $R_{11}'$ substituent(s) may be located on any of the available carbon atoms of the benzene ring of the indolino portion of the compound, i.e., at the 4, 5, 6 or 7 positions.

It is possible that photochromic organic substances of graphic formula III (and IV) may be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole, or mixtures thereof. Thus, when "d" is 1, the photochromic substance may be substituted at the 4 position on the indoline ring, at the 6 position of that ring or comprise a mixture of such isomers. When "d" is 2, the $R_{11}'$ substituents may be present at any combination of the 4, 5, 6, or 7 carbon atoms of the indoline ring and may comprise an isomeric mixture of such compounds, e.g., a mixture of compounds having substituents at the 4 and 5, 4 and 6, 5 and 6, 4 and 7, 5 and 7, and 6 and 7 positions of the indoline ring. Commonly, when "d" is 2 the $R_{11}'$ substituents are located at the 4 and 5, or 5 and 6 positions. Also contemplated are materials containing mixtures of such isomers, e.g., materials comprising 4 (and Compound 2 in Table 2 may be named 1,3,3,4(and 6),5-pentamethyl-methoxy-spiro-[indolino-2,3′[3H]-naphth[2,1-b][1,4]-oxazine]. Similarly, compound 6 in Table 2 may be named 1,3,4 (and 6),5-tetramethyl-3-ethyl-9′-methoxyspiro [indolino-2,3′[3H]-naphth [2,1-b][1,4]-oxazine. Other compounds in Table 2 can be similarly named taking into account the different substituents. Moreover, compounds derived from the description of graphic formula IV may be similarly named.

Spiro(indolino) benzoxazines compounds described in U.S. Pat. No. 4,816,584 may be represented by the following graphic formula V.

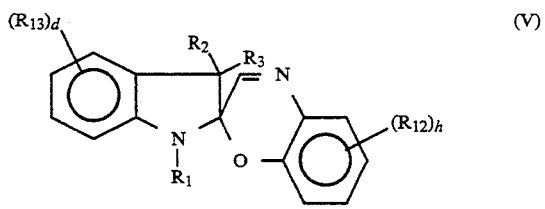

(V)

wherein $R_1$, $R_2$, $R_3$ and d are the same as described with respect to graphic formula II and $R_{12}$ and $R_{13}$ are each selected from the group consisting of $C_1$–$C_5$ alkyl, e.g., $C_1$–$C_2$ alkyl, $C_1$–$C_5$ alkoxy, e.g., $C_1$–$C_2$ alkoxy, preferably methoxy, and h is the integer 1 or 2.

When "h" is 1, the $R_{12}$ substituent may be located on any of the available carbon atoms of the benzene ring of the benzoxazine moiety, i.e., at the 5, 6, 7 or 8 positions. Preferably, the $R_{12}$ substituent is located at the number 5, 6, or 7 carbon atom. When "h" is 2, the $R_{12}$ substituents may be the same or different and in either case are selected from the above-described group. When "h" is 2, the $R_{12}$ substituents are desirably located at the 5 and 7 or 6 and 8 positions.

Examples of spiro(indolino)benzoxazines within the scope of graphic formula V are listed in Table 3. Compound 1 may be named: 7-methoxy-1′,3′,3′,4′ (and 6′), 5′-pentamethylspiro- [2H-1,4-benzoxazine-2,2′-indoline]. Compounds 2–6 may be similarly named as substituted spiro(indolino) benzoxazines using the substituents described in Table 3 for such compounds. Moreover, compounds derived from the description of graphic formula V may be similarly named. In naming the spiro(indoline)benzoxazines, the IUPAC rules of organic nomenclature have been used. The positions of the indolino portion of the molecule have been numbered counterclockwise starting with the nitrogen atom as the number one (1) position, and are identified by a prime number, e.g., 3′. The positions of the benzoxazine portion of the molecule have been numbered clockwise starting with the oxygen atom as the number one (1) position.

TABLE 3

| Compound No. | $R_1$ | $R_2$ | $R_3$ | $R_{13}$ | $R_{13}$ | $R_{12}$ | $R_{12}$ |
|---|---|---|---|---|---|---|---|
| 1 | Me | Me | Me | 4(6)-Me | 5-Me | 7-OMe | — |
| 2 | Me | Me | Me | 4(6)-Me | 5-Me | 7-OMe | 5-OMe |
| 3 | Me | Me | Me | 5-OMe | — | 7-OMe | 5-OMe |
| 4 | Me | Me | Me | 4(6)-Me | 5-Me | 7-OMe | 6-Ome |
| 5 | Me | Me | Et | — | — | 7-OMe | 5-OMe |

TABLE 3-continued

| Compound No. | $R_1$ | $R_2$ | $R_3$ | $R_{13}$ | $R_{13}$ | $R_{12}$ | $R_{12}$ |
|---|---|---|---|---|---|---|---|
| 6 | nBu | Me | Me | — | — | 7-OMe | 5-OMe |

Key:
Me = methyl
nBu = n-butyl
Et = ethyl
OMe = methoxy

The naphthopyran compounds of the present invention may be combined with or used in conjunction with photochromic amounts of a spiro(indolino) pyrido benzoxazine, or spiro(indolino) naphthoxazine compounds in amounts and in a ratio such that an organic host material to which the mixture of compounds is applied or in which they are incorporated exhibits a desired resultant color, e.g., a substantially neutral color such as shades of gray or brown, when activated with unfiltered sunlight, i.e., as near a neutral color as possible given the colors of the activated pyran and oxazine photochromic compounds. The relative amounts of the aforesaid oxazine and pyran compounds used will vary and depend in part upon the relative intensities of the color of the activated species of such compounds, and the ultimate color desired. Similarly, the naphthopyran compounds of the present invention may be combined with photochromic amounts of spiro(indolino)benzoxazine compounds in amounts and in a ratio such that an organic host material to which the mixture of compounds is applied or in which they are incorporated exhibits a near-brown color. Generally, the mole ratio of the aforedescribed spiro(indolino) oxazine compound(s) to the pyran compound(s) of the present invention will vary from about 1:3 to about 3:1, e.g., between about 1:1 and about 2:1.

In addition, it is contemplated that the naphthopyran compounds of the present invention may be admixed with photochromic amounts of other naphthopyran compounds, such as those described in U.S. Pat. No. 5,066,818, i.e., those compounds containing at least one ortho-substituted phenyl substituent at the 3-position of the pyran ring, preferably a monoortho-substituted phenyl substituent. Compounds described in U.S. Pat. No. 5,066,818 that are not substituted on the naphtho portion of the naphthopyran may be represented graphically by the following graphic formula,

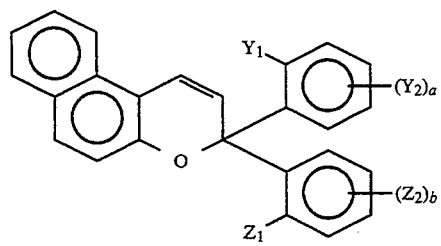

(VI)

wherein $Y_1$ may be selected from the group consisting of $C_1$–$C_5$ alkyl, $C_1$–$C_5$ alkoxy, fluoro and chloro. Preferably $Y_1$ is selected from the group consisting of $C_1$–$C_3$ alkyl, $C_1$–$C_3$ alkoxy and fluoro. $Z_1$ may be selected from the group consisting of hydrogen and $Y_1$. Each $Y_2$ and $Z_2$ may be selected from the group consisting of $C_1$–$C_5$ alkyl, $C_1$–$C_5$ alkoxy, cyano, hydroxy, halogen, preferably chloro or fluoro, acrylyl, methacrylyl, acryloxy 6) and 5-substituted spiro(indolino) pyrido benzoxazines.

Non-limiting examples of spiro(indolino) pyridobenzoxazines of graphic formula III are described in Table 1. Such pyridobenzoxazines are those in which $R_1$, $R_2$, $R_3$, and $R_{11}'$ are as indicated in Table 1, the letter "e" is 0 (zero), and the letter "d" is 0, 1 or 2. A hyphen (-) indicates the absence of a non-hydrogen substituent.

TABLE 1

| Compound/ | $R_1$ | $R_2$ | $R_3$ | $R_{11}'$ | $R_{11}'$ |
|---|---|---|---|---|---|
| 1 | CH₃ | CH₃ | CH₃ | — | — |
| 2 | CH₃ | CH₃ | CH₃ | 4(6)-CH₃ | 5-CH₃ |
| 3 | CH₃ | CH₃ | CH₃ | 5-OCH₃ | — |
| 4 | CH₃ | CH₃ | CH₃ | 5-Cl | 6-CH₃ |
| 5 | CH₃ | CH₃ | C₂H₅ | — | — |
| 6 | CH₃ | CH₃ | C₂H₅ | 5-CH₃ | 4(6)-CH₃ |
| 7 | CH₃ | C₂H₅ | C₂H₅ | — | — |
| 8 | n-C₄H₉ | CH₃ | C₂H₅ | — | — |
| 9 | CH₃ | CH₃ | phenyl | — | — |
| 10 | CH₃ | phenyl | phenyl | — | — |
| 11 | C₂H₅ | CH₃ | C₂H₅ | 4(6)-CH₃ | 5-CH₃ |
| 12 | n-C₄H₉ | CH₃ | C₂H₅ | 5-CH₃ | (4)6-CH₃ |
| 13 | CH₃ | CH₃ | CH₃ | 5-CH₃ | (4)6-CH₃ |
| 14 | n-C₃H₇ | CH₃ | CH₃ | 5-CH₃ | — |
| 15 | n-C₃H₇ | CH₃ | CH₃ | 5-OCH₃ | — |
| 16 | n-C₃H₇ | CH₃ | CH₃ | 4(6)-CH₃ | 5-CH₃ |

Compound 2 in Table 1 may be named 1,3,3,4(and 6),5-pentamethylspiro-[indolino-2,3'[3H]pyrido [3,2-f][1,4]benzoxazine]. Similarly, compound 6 in Table 1 may be named 1,3,4(and 6),5-tetramethyl-3-ethylspiro-[indolino-2,3'[3H]pyrido [3,2-f][1,4]benzoxazine]. Other compounds in Table 1 may be similarly named taking into account the different substituents. Moreover, compounds derived from the description of graphic formula III may be similarly named by substituting the substituents described with respect to $R_1$, $R_2$, $R_3$, $R_4'$ and $R_{11}'$ for those found in the description and in Table 1. When the letter "e" is 1 or more, the $R_4'$ substituent(s) are given a prime (') designation. For nomenclature purposes, numbering of the pyrido benzoxazine portion of the molecule is counter clockwise starting with the nitrogen atom of the oxazine ring as the number 1' position. Numbering of the indolino portion of the molecule is counter clockwise starting with the nitrogen atom as the number 1 position.

Spiro(indolino)naphthoxazines that may be used in the practice of the present process may be represented by the following graphic formula:

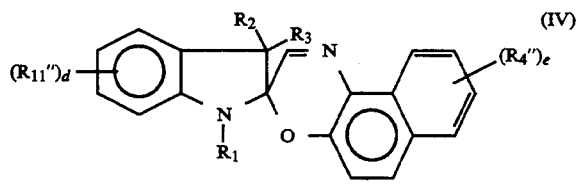

(IV)

wherein $R_1$, $R_2$ and $R_3$ are the same as that described with respect to graphic formula II.

Each $R_4''$ substituent in graphic formula IV may be selected from the group consisting of halogen, e.g., chloro, fluoro, or bromo, $C_1$-$C_5$ alkyl, $C_1$-$C_5$ alkoxy (e.g., methoxy, ethoxy, propoxy, butoxy and pentoxy), nitro, cyano, thiocyano, $C_1$-$C_4$ monohaloalkyl, e.g., $C_1$-$C_4$ monochloroalkyl, such as chloromethyl and chloroethyl, $C_1$-$C_2$ polyhaloalkyl, as for example, trihaloalkyl, such as trichloroalkyl or trifluoroalkyl, e.g., trifluoromethyl and 2,2,2-trifluoroethyl, and monoalkylamino or dialkylamino, wherein the alkyl moiety of the alkylamino group contains from 1 to 4 carbon atoms, e.g., methylamino, ethylamino, propylamino, dimethylamino and diethylamino. More particularly, the $R_4''$ substituent may be selected from the group $C_1$-$C_2$ alkyl, $C_1$-$C_2$ alkoxy, chloro, fluoro, bromo, nitro and trifluoromethyl. The letter "e" in graphic formula IV is an integer from 0 to 2, e.g., 1 or 2, and denotes the number of non-hydrogen $R_4''$ substituents. When "e" is 0, there are no $R_4''$ substituents and all of the aromatic carbon atoms of the naphtho moiety of the molecule represented by formula IV have their full complement of hydrogen atoms for the naphtho group shown.

As in the case with graphic formula III, when "e" is 1, the $R_4''$ substituent may be located on any of the available carbon atoms of the naphtho moiety of the naphthoxazine portion of the molecule, i.e., at the 5', 6', 7', 8', 9' or 10' positions. Preferably, the $R_4''$ substituent is present on the 7', 8' or 9' carbon atoms. When "e" is 2, the $R_4''$ substituents may be same or different and in either case are selected from the above-described group. When "e" is 2, the $R_4''$ substituents are commonly located at the 7' and 9', or 8' and 10' positions. For nomenclature purposes, numbering of spiro(indolino) naphthoxazines is the same as that described with regard to the spiro(indolino) pyrido benzoxazines of graphic formula III. $R_{11}''$ and the letter "d" in graphic formula IV are the same as that described with respect to $R_{11}$ and d in graphic formula II.

Non-limiting examples of spiro(indolino) naphthoxazines selected from the description of graphic formula IV are described in Table 2. Such spiro(indolino) naphthoxazines are those in which $R_1$, $R_2$, $R_3$, $R_4''$ and $R_{11}''$ are as indicated in Table 2, the letter "d" is 0, 1 or 2 and the letter "e" is 1. As in Table 1, a hyphen (-) indicates the absence of a non-hydrogen substituent. In Table 2, all of the $R_4''$ substituents are at the 9' carbon position.

TABLE 2

| Compound/ | $R_1$ | $R_2$ | $R_3$ | $R_4''$ (9''-) | $R_{11}''$ | $R_{11}''$ |
|---|---|---|---|---|---|---|
| 1 | CH₃ | CH₃ | CH₃ | OCH₃ | — | — |
| 2 | CH₃ | CH₃ | CH₃ | OCH₃ | 5-CH₃ | (4)4-CH₃ |
| 3 | CH₃ | CH₃ | CH₃ | OCH₃ | 5-OCH₃ | — |
| 4 | CH₃ | CH₃ | CH₃ | OCH₃ | 5-Cl | (4)6-CH₃ |
| 5 | CH₃ | CH₃ | C₂H₅ | OCH₃ | — | — |
| 6 | CH₃ | CH₃ | C₂H₅ | OCH₃ | 5-CH₃ | (4)6-CH₃ |
| 7 | CH₃ | C₂H₅ | C₂H₅ | OCH₃ | — | — |
| 8 | n-C₄H₉ | CH₃ | C₂H₅ | OCH₃ | — | — |
| 9 | CH₃ | CH₃ | phenyl | OCH₃ | — | — |
| 10 | CH₃ | phenyl | phenyl | OCH₃ | — | — |
| 11 | CH₃ | p-C₆H₄OCH₃ | p-C₆H₄OCH₃ | OCH₃ | — | — |
| 12 | C₂H₅ | CH₃ | C₂H₅ | OCH₃ | 5-CH₃ | — |
| 13 | n-C₄H₉ | CH₃ | C₂H₅ | OCH₃ | 5-CH₃ | — |

($C_1$–$C_4$) alkyl, and methacryloxy ($C_1$–$C_4$) alkyl. Preferably, each $Y_2$ and $Z_2$ are selected from the group consisting of $C_1$–$C_3$ alkyl, $C_1$–$C_3$ alkoxy and fluoro. The letters a and b in graphic formula VI are each an integer selected from the group consisting of 0, 1 or 2. When a or b are 0 (zero), the phenyl groups have their appropriate complement of ring hydrogens.

In a particular embodiment described in U.S. Pat. No. 5,066,818, $Y_1$ is $C_1$–$C_3$ alkyl, $C_1$–$C_3$ alkoxy and fluoro, $Z_1$ is hydrogen, $Y_2$ is $C_1$–$C_3$ alkoxy or hydrogen, $Z_2$ is selected from the group consisting of $C_1$–$C_3$ alkoxy, $C_1$–$C_3$ alkyl and hydrogen, a is 0 or 1 and b is 0, 1 or 2. While $Y_2$ and $Z_2$ substituents may be located at any of the unsubstituted portions of their respective phenyl groups, they are preferably in the 3, 4 or 5 positions. When a or b is 1. the substituent is preferably meta or para to the carbon atom attached to the pyran ring. When a or b is 2, the substituents preferably are located at the 3 and 4, 3 and 5 or 4 and 5 numbered carbon atoms. The mole ratio of the naphthopyrans of the present invention to those described in U.S. Pat. No. 5,066,818, i.e., those not substituted on the number 8 carbon atom, may vary from 1:3 to 3:1, e.g., between 1:1 and about 2:1.

Specific compounds described in U.S. Pat. No. 5,066,818 include:

(1) 3(2-fluorophenyl)-3(4-methoxyphenyl)-3H-naphtho[2,1-b]pyran.

(2) 3(2-fluorophenyl)-3(3,4-dimethoxyphenyl)-3H-naphtho[2,1-b]pyran.

(3) 3(2-methyl-4-methoxyphenyl)-3(4-methoxyphenyl)-3H-naphtho[2,1-b]pyran.

(4) 3(2-methylphenyl)-3(4-methoxyphenyl)-3H-naphtho[2,1-b]pyran.

(5) 3-phenyl-3(2,4-dimethoxyphenyl)-BH-naphtho[2,1-b]pyran.

(6) 3(4-methoxyphenyl)-3(2,4-dimethoxyphenyl)-3H-naphtho[2,1-b]pyran.

(7) 3(2,6-difluorophenyl)-3,(4-methoxyphenyl)-3H-naphtho[2,1-b]pyran.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

Singlet oxygen quenchers that may be used as stabilizers include complexes of nickel(2+), i.e., $Ni^{2+}$, with an organic ligand, cobalt (III) tris-di-n-butyldithiocarbamate, cobalt (II) diisopropyldithiocarbamate, and nickel diisopropyldithiophosphate. Such singlet oxygen quenchers are used in stabilizing amounts.

Preferred are complexes of $Ni^{2+}$ such as [2,2-thiobis[4-(1,1,3,3-tetramethylbutyl) phenolato](-butylamine)]nickel, which is sold under the tradename of CYASORB UV 1084; nickel [0-ethyl(3,5-di-tert-butyl-4-hydroxybenzyl)]phosphonate, which is sold under the tradename IRGASTAB 2002; nickel dibutyldithiocarbamate, which is sold under the tradename RYLEX NBC; bis[2,2'-thiobis-4-(1,1,3,3-tetramethylbutyl)phenolato]nickel, which is sold under the tradename UV-CHEK AM 101; nickel di-isopropyl dithiophosphate and other $Ni^{2+}$ complexes sold under the tradenames of UV-CHEK AM 105, UV-CHEK 126, and UV-CHEK AM 205.

Hindered amine light stabilizers that may be used include bis(2,2,6,6-tetramethyl-4-piperidinyl) sebacate, which is sold under the tradename TINUVIN 770; bis(1,2,2,6,6-pentamethyl-4-piperidinyl) sebacate, which is sold under the tradename TINUVIN 765; di(1,2,2,6,6-pentamethyl-4-piperidinyl)butyl- (3',5'-ditertiarybutyl-4-hydroxybenzyl)malonate, which is sold under the tradename TINUVIN 144; poly[(6-[(1,1,3,3-tetramethylbutyl)amino]1,3,5-triazine-2,4-diyl)-(6-[2,2,6,6-tetramethyl-4-piperidinyl]-amino-hexamethylene)], which is sold under the tradename CHIMASSORB 944; and poly[[6-(morpholino)-s-triazine-2,4-diyl][16-(2,2,6,6-tetramethyl-4-piperdyl)amino]hexamethylene], which is sold under the tradename CYASORB 3346. Other hindered amine light stabilizers that may be used are those sold under the tradename TINUVIN 622, SPINUVEX A-36 and HOSTAVIN TMN 20. Such stabilizers are used in stabilizing amounts.

The foregoing singlet oxygen quenchers and hindered amine light stabilizers may be used singly or in combination in amounts sufficient to enhance the light-fatigue resistance of the photochromic substance(s) described herein. Between 0.01 and about 5 percent weight of the foregoing stabilizers may be used (alone or in combination) to improve the light fatigue resistance of the photochromic materials.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance. i.e., so the change in color is readily apparent to the observer. Preferably, the host material article is a solid transparent or optically clear material, e.g., materials suitable for optical applications, such as plano and ophthalmic lenses, windows, automotive transparencies, e.g., windshields, aircraft transparencies, plastic sheeting, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a polycarbonate resin, such as the carbonate-linked thermoplastic resin derived from a bisphenol, such as bigphenol A, and phosgene, which is sold under the trademark, LEXAN, i.e., poly(4-phenoxy-4'-phenoxycarbonyl-2,2-propane); a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80-85 percent of the bis(allyl carbonate) and 15-20 percent vinyl acetate, and copolymers with a polyurethane having terminal diacrylate functionality, as described in U.S. Pat. No. 4,360,653; cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bigphenol bis(allyl carbonate) compounds. These monomers can be described as unsaturated polycarbonates of polyols, e.g, glycols. The monomers can be prepared by procedures well known in the art, e.g., methods described in U.S. Pat. Nos. 2,370,567 and 2,403,113.

The aforedescribed polyol (allyl carbonate) monomers may be represented by the graphic formula:

wherein R is the radical derived from an unsaturated alcohol and is commonly an allyl or substituted allyl group, R' is the radical derived from the polyol, and n is a whole number from 2–5, preferably 2. The allyl group (R) may be substituted at the 2 position with a halogen, most notably chlorine or bromine, or an alkyl group containing from 1 to 4 carbon atoms, generally a methyl or ethyl group. The R group may be represented further by the graphic formula:

wherein $R_o$ is hydrogen, halogen, or a $C_1$–$C_4$ alkyl group. Specific examples of R include the groups: allyl, 2-chloroallyl, 2-bromoallyl, 2-fluoroallyl, 2-methylallyl, 2-ethylallyl, 2-isopropylallyl, 2-n-propylallyl, and 2-n-butylallyl. Most commonly R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

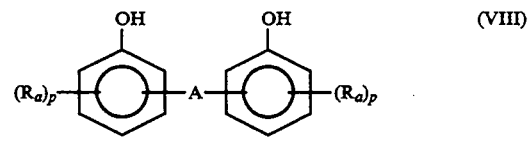

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), $R_a$ represents lower alkyl substituents of from 1 to 3 carbon atoms and halogen, e.g., chlorine and bromine, and p is the integer 0, 1, 2, or 3. Preferably, the hydroxyl group is in the ortho or para position.

Specific examples of the radical R' include: alkylene groups containing from 2 to 10 carbon atoms such as ethylene, ($-CH_2-CH_2-$), trimethylene, methylethylene, tetramethylene, ethylethylene, pentamethylene, hexamethylene, 2-methylhexamethylene, octamethylene, and decamethylene; alkylene ether groups such as —CH$_2$—O—CH$_2$—, —CH$_2$CH$_2$—O—CH$_2$CH$_2$—, —CH$_2$—O—CH$_2$—, and —CH$_2$CH$_2$CH$_2$—O—CH$_2$CH$_2$CH$_2$—; alkylene polyether groups such as —CH$_2$CH$_2$—O—CH$_2$CH$_2$—O—CH$_2$CH$_2$—, and —CH$_2$CH$_2$CH$_2$—O—CH$_2$CH$_2$CH$_2$—O—CH$_2$CH$_2$CH$_2$—; alkylene carbonate and alkylene ether carbonate groups such as —CH$_2$CH$_2$—O—CO—O—CH$_2$CH$_2$— and —CH$_2$CH$_2$—O—CH$_2$CH$_2$—O—CO—O—CH$_2$CH$_2$—O—CH$_2$CH$_2$—; and isopropylidene bis(para-phenyl), i.e.,

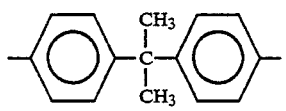

Most commonly, R' is —CH$_2$CH$_2$—, —CH$_2$CH$_2$—O—CH$_2$CH$_2$—, or —CH$_2$CH$_2$—O—CH$_2$CH$_2$—O—CH$_2$CH$_2$—.

Specific non-limiting examples of polyol (allyl carbonate) monomers include ethylene glycol bis (2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis (2-ethylallyl carbonate), 1,3-propanediol bis (allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which may be utilized to prepare a transparent host material are:

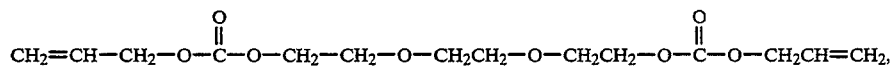

Triethylene Glycol bis(Allyl Carbonate)

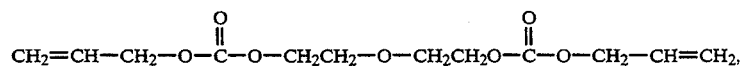

Diethylene Glycol bis(Allyl Carbonate)

and

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

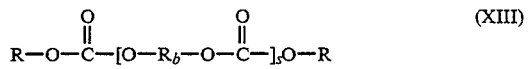

wherein R is as defined above, R$_b$ is a bivalent radical, e.g., alkylene or phenylene, derived from a diol, and s is a whole number from 2 to 5. The related monomer species of diethylene glycol bis(allyl carbonate) can be represented by the graphic formula,

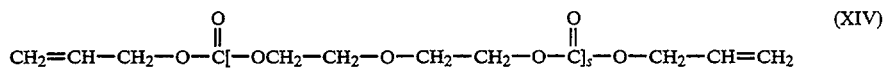

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4, etc.

In addition, a partially polymerized form of the polyol (allyl carbonate) monomer, i.e., prepolymer, can be used. In that embodiment, the monomer is thickened by heating or partially polymerized by using small, e.g., 0.5–1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

Polyfunctional acrylate monomers that may be used to prepare synthetic polymeric host materials are esterification products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

wherein R$_t$ is hydrogen or methyl, n is the number 2, 3, or 4, and R'' is the multivalent radical, i.e., a bivalent, trivalent or quadravalent radical, remaining after removal of the hydroxy groups from a polyol, having from 2 to 4 hydroxy groups, e.g., a diol, a triol or tetracarbinol respectively. More particularly, $R_t$ is hydrogen or methyl, and n is 2 or 3, more usually 2.

R" may be selected from the group consisting of alpha, omega $C_2$–$C_8$ glycols, cyclohexane diol, diethylene glycol, triethylene glycol, tetraethylene glycol, dipropylene glycol, $C_2$–$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2$=CH—) grouping. Such compatible monomers include monofunctional acrylic and methacrylic acid esters, and vinyl esters of $C_2$–$C_6$ carboxylic acids, i.e., vinyl carboxylates. Preferably, the copolymerizable monomer is a non-aromatic, e.g., non-benzenoid, containing monomer. Monofunctional acrylic or methacrylic ester monomers may be graphically illustrated by the following formula, $$CH_2=C(R_t)-C(O)-O-R''' \qquad (XVI)$$

wherein $R_t$ is hydrogen or methyl, and R''' is selected from the group consisting of $C_1$–$C_{12}$, e.g., $C_1$–$C_8$, alkyl, $C_5$–$C_6$ cycloalkyl, glycidyl and hydroxyethyl. Preferably, R''' is a $C_1$–$C_4$ alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, 1, dl)) and ethylene glycol. Examples of vinyl carboxylates include vinyl acetate, vinyl propionate, vinyl butyrate and vinyl valerate. In addition to and/or in place of the aforedescribed monofunctional copolymerizable monomer, monofunctional allylic and difunctional allylic copolymerizable compatible monomers may also replace a portion of the polyfunctional acrylate monomer. Monofunctional allylic monomers contemplated include allyl esters of $C_2$–$C_6$ carboxylic acids, $C_1$–$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula VI.

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity. Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material.

The present invention is more particularly described in the following examples which are intended as illustrative only, since numerous modifications and variations therein will be apparent to those skilled in the art.

EXAMPLE 1

A reaction flask was charged with 200 milliliters (ml) of acetone, 13.8 grams (g) (0.1 mole) of powdered potassium carbonate and 16.0 g (0.1 mole) of 2,6-dihydroxynaphthalene. 12.6 g (0.1 mole) of dimethylsulfate was added dropwise and the reaction mixture was stirred at room temperature for 72 hours under a nitrogen atmosphere. 200 ml of a 10% aqueous sodium hydroxide solution was then added to the reaction flask. A white precipitate that formed, was removed by vacuum filtration. The aqueous filtrate was acidified with hydrochloric acid to a pH of 3 and the aqueous solution extracted three times—each time with 100 ml of methylene chloride. The extracts were combined, dried over anhydrous magnesium sulfate for 10 minutes and the solvent removed under vacuum. The remaining solid was washed with hot water—yielding 3.0 g of a solid product, which was confirmed by NMR spectroscopy to be 6-methoxy-2-hydroxynaphthalene.

1.1 g (0.006 mole) of the aforedescribed product, 6-methoxy-2-hydroxynaphthalene, was added to a reaction flask containing 100 ml of benzene and 1.3 g (0.006 mole) of 1,1-diphenyl-2-propyn-1-ol. A catalytic amount (approximately 20.0 milligrams) of p-toluene sulfonic acid was added, the resulting mixture stirred and placed under a nitrogen atmosphere. The reaction mixture was heated gently at 50° C. for 4 hours, and then 200 ml of a 10% aqueous sodium hydroxide solution was added to the reaction flask. After stirring for 15 minutes, the reaction mixture was extracted twice—each time with 100 ml of methylene chloride. The extracts were combined, dried over anhydrous magnesium sulfate and the solvent removed under vacuum. The product (1.0 grams) melted at 173–175° C. An NMR spectrum confirmed the product to be 8-methoxy-3,3-diphenyl-3H-naphtho [2,1-b]pyran.

EXAMPLE 2

A reaction flask was charged with 8.0 g of 2-fluoro-4'-methoxybenzophenone, (prepared by the Friedel-Crafts reaction of 2-fluorobenzoylchloride with anisole) in 150 ml of tetrahydrofuran and 14.0 g (1.5 equivalents) of sodium acetylide. The reaction mixture was stirred under a nitrogen atmosphere for 72 hours, cooled by pouring it into a 500 ml beaker containing ice water and extracted three times—each time with 100 ml of methylene chloride. The extracts were combined, dried over anhydrous magnesium sulfate and the solvent removed by vacuum. The product (7.0 g) was a yellow oil. The structure was confirmed by NMR to be 1-(2-fluorophenyl)-1-(4-methoxyphenyl)-2-propyn-1-ol.

2.4 g (0.008 mole) of the aforedescribed product, 1-(2-fluorophenyl)-1-(4-methoxyphenyl)-2-propyn-1-ol, was added to a reaction flask containing 100 ml of benzene and 1.4 g (0.008 mole) of 6-methoxy-2-hydroxynaphthalene. A catalytic amount of p-toluene sulfonic acid (approximately 20.0 milligrams) was added and the resulting mixture stirred and heated between 30–35° C. under a nitrogen atmosphere for 3 hours. The reaction mixture was transferred to a solution containing 20% aqueous sodium hydroxide and extracted three times—each time with 100 ml of methylene chloride. The extracts were combined, dried over anhydrous magnesium sulfate and the solvent removed under vacuum. The resultant oil was column chromatographed on silica using 1:10 mixture of ethyl acetate:hexane as the elutant and crystallized by cooling in diethyl ether. The product (0.5 g) melted at 120–123° C. An NMR spectrum confirmed the product to be 8-methoxy-3-(2-fluorophenyl)-3-(4-methoxyphenyl)-3H-naphtho[2,1-b]pyran.

EXAMPLE 3

A reaction flask was charged with 5 g (0.025 mole) of 4-methylbenzophenone, (prepared by the Friedel-Crafts reaction of benzoylchloride with toluene) in 200 ml of tetrahydrofuran and with 8.2 g (0.03 mole) of sodium acetylide. The reaction mixture was stirred under a nitrogen atmosphere for 8 hours, after which the reaction mixture was quenched in ice water and extracted three times—each time with 100 ml of diethyl ether. The extracts were combined, dried over anhydrous magnesium sulfate, and the solvent removed under vacuum. The product (5.0 g) was confirmed by NMR spectroscopy to be 1-phenyl-1-(4-methylphenyl)-2-propyn-1-ol.

5.0 g (0.02 mole) of the aforedescribed product, 1-phenyl-1-(4-methylphenyl)-2-propyn-1-ol, was added to a reaction flask containing 3.0 g (0.02 mole) of 6-methoxy-2-hydroxynaphthalene and 200 ml of benzene. The mixture was stirred under a nitrogen atmosphere, at 35° C. for 4 hours. The solvent was removed on a rotary evaporator and the resulting crude oil was washed with 200 ml of a 10% aqueous sodium hydroxide solution. The aqueous phase was extracted three times—each time with 100 ml of diethyl ether. The extracts were combined and dried over anhydrous magnesium sulfate for 15 minutes. The solvent was removed under vacuum and the resulting oil was crystallized using an ether-hexane mixture. The product crystals (3.0 g) melted at 169–171° C. An NMR spectrum confirmed the product to be 8-methoxy-3-phenyl-3-(4-methylphenyl)3H-naphtho[2,1-b]pyran.

EXAMPLE 4

A reaction flask was charged with 5.0 g (0.02 mole) of 4-trifluoromethylbenzophenone, 200 ml of tetrahydrofuran and 6.7 g (0.024 mole) of sodium acetylide. The reaction mixture was stirred for 72 hours under a nitrogen atmosphere at room temperature and then was poured into a 500 ml beaker containing ice water and stirred for an additional thirty minutes. The aqueous phase was extracted three times—each time with 100 ml of diethyl ether. The extracts were combined and dried over anhydrous magnesium sulfate for 5 minutes. The solids were filtered and the solvent removed under vacuum. The product (2.75 g) was a yellow oil. The structure was confirmed by NMR spectroscopy to be 1-phenyl-1-(4-trifluoromethylphenyl)-2-propynl-1-ol.

2.75 g (0.01 mole) of the aforedescribed product, 1-phenyl-1-(4-trifluoromethylphenyl)-2-propynl-1-ol, was added to a reaction flask containing 1.9 g (0.01 mole) of 6-methoxy-2-hydroxynaphthalene and 200 ml of benzene. A catalytic amount (approximately 20.0 milligrams) of p-toluene sulfonic acid was added and the mixture was heated to 35° C. with stirring under a nitrogen atmosphere for 10 hours. The reaction mixture was transferred to a 500 ml beaker containing a 10% aqueous sodium hydroxide solution and stirred for an additional thirty minutes. The organic layer was separated and the aqueous layer extracted twice—each time with 100 ml of methylene chloride. The extracts were combined and dried over anhydrous magnesium sulfate for 10 minutes. After filtering off the solids, the solvent was removed under vacuum to yield 3.0 g of an oil. This oil was column chromatographed on silica gel using 20% ethyl acetate-hexane as the elutant. The solvent was removed under vacuum and the product was crystallized from hexane. The product (0.5 g) melted at 155–157° C. The structure was confirmed by NMR spectroscopy to be 8-methoxy-3-phenyl-3-(4-trifluoromethylphenyl)-3H-naphtho[2,1-b]pyran.

EXAMPLE 5

A reaction flask was charged with 5.5 g (0.023 mole) of 2-fluoro-4′-methylbenzophenone, (prepared by the Friedel-Crafts reaction of 2-fluorobenzoylchloride with toluene) in 200 ml of tetrahydrofuran and with 7.5 g (0.023 mole) of sodium acetylide. The reaction mixture was stirred for 24 hours, then quenched with ice water and stirred for an additional thirty minutes. The organic phase was separated and the aqueous phase was extracted three times—each time with 100 ml of methylene chloride. The extracts were combined and washed with distilled water until clear. The extracts were dried over anhydrous magnesium sulfate, and the solvent removed under vacuum. The product (5.5 g) was a yellow oil. NMR spectroscopy confirmed the product to be 1-(2-fluorophenyl)-1-(4-methylphenyl)-2-propyn-1-ol.

5.5 g (0.023 mole) of the aforedescribed product, 1-(2-fluorophenyl)-1-(4-methylphenyl)-2-propyn-1-ol, was added to a reaction flask containing 4.0 g (0.023 mole) of 6-methoxy-2-hydroxynaphthalene and 200 ml of benzene. A catalytic amount (approximately 20.0 milligrams) of p-toluene sulfonic acid was added with stirring and the reaction was heated at 40° C. under a nitrogen atmosphere for 6 hours. The reaction mixture was transferred to a beaker containing 200 ml of a 10% aqueous sodium hydroxide solution and stirred for 15 minutes. The organic phase was separated and the aqueous phase washed twice—each time with 100 ml of methylene chloride. The extracts were combined, dried over anhydrous magnesium sulfate and the solvent removed under vacuum. The resultant oil was column chromatographed on silica gel using 20% ethyl acetate—hexane as the elutant. The photochromic fractions were collected and the solvent removed under vacuum. The product (2.0 g) melted at 157–160° C. NMR spectroscopy confirmed the product to be 8- methoxy-3-(2-fluorophenyl)-3-(4-methylphenyl)-3H-naphtho[2,1-b]pyran.

EXAMPLE 6

A reaction flask was charged with 5.0 g (0.02 mole) of 4-(dimethylamino) benzophenone, 200 ml of tetrahydrofuran and 9.3 g (0.03 moles) of sodium acetylide. The reaction mixture was stirred for 24 hours under a nitrogen atmosphere. 3.1 g (0.01 moles ) of additional sodium acetylide were added each time to the reaction mixture after elapsed times of 8 and 16 hours. The reaction mixture was stirred an additional 24 hours, then transferred to a beaker containing a mixture of distilled water and methylene chloride and stirred for 10 minutes. The organic layer was separated and the aqueous layer was extracted twice—each time with 100 ml of methylene chloride. The extracts were combined, dried over anhydrous magnesium sulfate and the solvent removed under vacuum. The product was crystallized using a hexane/ether mixture. The product (4.2 g) melted at 121–123° C. NMR spectroscopy confirmed the product to be 1-(phenyl)-1-(4-dimethylaminophenyl)-2-propyn-1-ol.

2.0 g ( 0.008 moles) of the aforedescribed product, 1-(phenyl)-1-(4-dimethylaminophenyl)-2-propyn-1-ol, was added to a reaction flask containing 1.56 g (0.009 mole) of 6-methoxy-2-hydroxynaphthalene and 150 ml of benzene. 5.0 g of acidic alumina was added and the reaction mixture stirred for one hour at room temperature under a nitrogen atmosphere. The reaction mixture was heated on a steam bath for an additional forty-five minutes. The reaction mixture was vacuum filtered to remove the alumina which was washed with 200 ml of ethyl acetate. The ethyl acetate was washed with 250 ml of a 10% aqueous sodium hydroxide solution, dried over anhydrous magnesium sulfate and the solvent was removed under vacuum. The resultant product was crystallized in an ether/hexane mixture. The product (2.0 g) melted at a temperature greater than 225° C. The structure was confirmed by NMR spectroscopy to be 8-methoxy-3-(4-dimethylaminophenyl)-3-(phenyl)-3H-naphtho[2,1-b]pyran.

EXAMPLE 7

A 500 ml round bottom reaction flask was charged with 4.0 g (0.025 mole) of 2,6-dihydroxynaphthalene, 200 ml of methylene chloride and 2.6 g (0.025 mole) of acetic anhydride. One equivalent of triethylamine was slowly added with stirring. After stirring for an additional one hour, dilute hydrochloric acid (200 ml) was added and unreacted 2,6-dihydroxynaphthalene removed by vacuum filtration. The organic phase was separated and the aqueous phase extracted three times, each time with 100 ml of methylene chloride. The extracts were combined, dried and solvent removed under vacuum. The resulting crude oil was a 50—50 mixture of 6-acetoxy-2-hydroxynaphthalene and 2,6-diacetoxynaphthalene.

The crude oil (4.0 g) was mixed with 200 ml of benzene and 2.08 g (0.01 mole) of 1,1-diphenyl-2-propyn-1-ol. A catalytic amount (about 20.0 milligrams) of p-toluene sulfonic acid was added to the mixture with stirring. After 4 hours, a 5 weight percent sodium hydroxide solution was added, the organic phase separated and the aqueous phase extracted three times, each time with 100 ml of methylene chloride. The extracts were combined, dried and solvent removed under vacuum to yield a crude yellow oil. The crude oil was column chromatographed on silica gel using chloroform as the elutant. The solvent was removed from the combined photochromic fractions to yield a crystalline product having a melting point of 180–182° C. and an assay of 97.7%. NMR spectroscopy confirmed the product to be 8-acetoxy-3,3-diphenyl-3H-naphtho[2,1-b]pyran.

EXAMPLE 8

In addition to the products cited in Examples 1–6, the following compounds were prepared using methods of synthesis similar to those stated in the Examples:

Compound A - 3,3-diphenyl-3H-naphtho[2,1-b]pyran,

Compound B - 5-methoxy-3,3-diphenyl-3H-naphtho[2,1-b]pyran,

Compound C - 7-methoxy-3,3-diphenyl-3H-naphtho[2,1-b]pyran,

Compound D - 9-methoxy-3,3-diphenyl-3H-naphtho[2,1-b]pyran,

Compound E - 3-(2-fluorophenyl)-3-(4-methoxyphenyl)-3H-naphtho[2,1-b]pyran.

EXAMPLE 9

All of the compounds of Examples 1–8 were imbibed by thermal transfer into test samples of a homopolymer of diethylene glycol bis(allyl carbonate) by the following procedure. Each naphthopyran was dissolved in toluene solvent to form a 4% solution of the compound. A piece of No. 4 Whatman filter paper was saturated with the naphthopyran solution and allowed to air dry. The dried filter paper was placed on one side of the polymer test sample, which measured ⅛ inch (0.3 centimeter)×2 inch (5.1 centimeters)×2 inch (5.1 centimeters). A piece of untreated filter paper was placed on the other side of the polymer test sample and the resulting sandwich placed between two plates of flat aluminum metal plates. The entire assembly was then placed in a 155° C. oven for a time sufficient to thermally transfer the naphthopyran into the polymer test sample. Residence times in the oven were adjusted to imbibe comparable amounts of the naphthopyran compounds, as measured by UV absorbance.

The imbibed test samples were removed from the oven, washed with acetone, and tested for photochromic response rates on an optical bench. The samples were illuminated by a filtered 150 watt Xenon lamp fitted with a copper sulfate bath. An OX1 filter with a half-power band width of 320–380 nm was used in conjunction with quartz metallized neutral density filters to provide a total UV irradiance level of 3.0 mW/cm$^2$ as measured using a calibrated radiometer at a position corresponding to the illuminated surface of the sample.

This UV-irradiance level is equivalent to approximately 0.8 sun of a clear noon, July sunshine measured at latitude 41° 10'N using the calibrated radiometer. Control of exposure was facilitated by means of a shutter placed at the exit lens of the Xenon arc lamp housing. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

The ΔOD/Min, which represents the sensitivity of the photochromic compound's response to UV light, was measured using photopic filters on the silicon detector. The response of the filtered detector approximated the luminosity curve. The ΔOD was measured over the first five (5) seconds of UV exposure, then expressed on a per minute basis. The saturation optical density (OD) was taken under identical conditions as the ΔOD/Min, except UV exposure was continued for 20 minutes.

The lambda max (UV) reported in Table 4 is the wavelength in the ultraviolet range closest to the visible spectrum. The lambda max (visible) is the wavelength in the visible spectrum at which the maximum absorption of the activated (colored) form of she photochromic compound occurs. The shift in Lambda Max (UV) also results in an unexpected increase in Sensitivity and Saturation OD (compare the data for Example 1 versus the unsubstituted analog of Example 8A, as well as Example 2 versus Example 8E). Results are tabulated in Table 4.

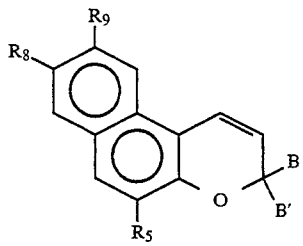

wherein $R_5$ and $R_9$ are each selected from the group consisting of hydrogen, $C_1$-$C_4$ alkoxy and $C_1$-$C_4$ alkyl, $R_8$ is selected from the group consisting of halogen, $C_1$-$C_5$ acyloxy, benzoyloxy, methoxybenzoyloxy, di(C$_1$-C$_5$)alkylamino, and LO—, wherein L is a $C_1$-$C_{12}$ alkyl, $C_6$-$C_9$ aryl($C_1$-$C_3$)alkyl, $C_5$-$C_7$ cycloalkyl, or $C_1$-$C_4$ alkyl substituted $C_5$-$C_7$ cycloalkyl, and wherein (i) B is selected from the group consisting of unsubsti-

TABLE 4

| EXAMPLE COMPOUNDS | LAMBDA MAX (VISIBLE) | LAMBDA MAX (UV) | ΔOD/MIN SENSITIVITY | ΔOD @ SATURATION |
|---|---|---|---|---|
| 1 | 473 | 376 | 1.25 | 0.73 |
| 2 | 480 | 376 | 1.21 | 1.46 |
| 3 | 472 | 377 | 0.98 | 0.53 |
| 4 | 467 | 376 | 0.94 | 0.67 |
| 5 | 473 | 375 | 1.12 | 1.47 |
| 6 | 543 | 376 | — | — |
| 7 | 446 | 365 | 0.72 | 0.32 |
| 8A | 430 | 359 | 0.87 | 0.36 |
| 8B | 432 | 323 | 0.49 | 0.46 |
| 8C | 432 | 365 | 0.92 | 0.39 |
| 8D | 426 | 329 | 0.62 | 0.31 |
| 8E | 456 | 359 | 0.98 | 1.00 |

The results of Table 4 show that Compounds 8B, 8C and 8D, which were respectively substituted with a methoxy substituent at the number five, seven and nine carbon atoms on the naphtho portion of the naphthopyran compound, exhibited no significant increase in the measured parameters over the unsubstituted analogous Compound 8A. Compound 1, which was substituted with a methoxy substituent at the number eight carbon atom on the naphtho portion of the naphthopyran compound, demonstrated a surprisingly unexpected increase in all the measured parameters compared to the results obtained for Compounds 8A, 8B ,8C and 8D. Further substitution on the diaryl moieties of Compound 1, i.e., the diphenyl moieties, yielded Compounds 2-6. These compounds also had higher measured results than those obtained for Compounds 8A, 8B , 8C and 8D. Compound 7, which had a substituent different than methoxy at the number 8 carbon atom on the naphtho portion of the naphthopyran compound also exhibited a bathochromic shift in the visible spectrum, but not as large as that of compound 1.

Although the present invention has been described with reference to the specific details of particular embodiments thereof, it is not intended that such details be regarded as limitations upon the scope of the invention except as and to the extent that they are included in the accompanying claims.

I claim:

1. A naphthopyran represented by the following graphic formula:

tuted or substituted phenyl, and B' is selected from the group consisting of the unsubstituted or substituted heterocyclic aromatic groups pyridyl, thienyl, benzothienyl, furyl, and benzofuryl, or (ii) B and B' taken together form the adamantyl group, said aryl and heterocyclic group substituents each being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl, di($C_1$-$C_5$)alkylamino, and halogen, said halogen and halo substituents being selected from the group consisting of fluorine, chlorine and bromine.

2. A naphthopyran represented by the following graphic formula:

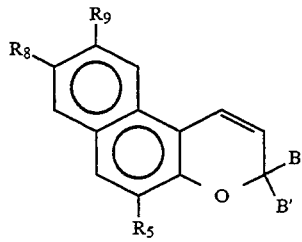

wherein $R_5$ and $R_9$ are each selected from the group consisting of hydrogen, $C_1$-$C_4$ alkoxy and $C_1$-$C_4$ alkyl, $R_8$ is selected from the group consisting of halogen, $C_1$-$C_5$ acyloxy, benzoyloxy, methoxybenzoyloxy, di(C$_1$-C$_5$)alkylamino, and LO—, wherein L is a $C_1$-$C_{12}$ alkyl, $C_6$-$C_9$ aryl($C_1$-$C_3$)alkyl, $C_5$-$C_7$ cycloalkyl, or $C_1$-$C_4$ alkyl substituted $C_5$-$C_7$ cycloalkyl, and wherein (i) B is a phenyl group represented by the following graphic formula:

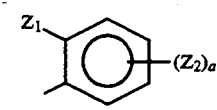

wherein $Z_1$ is selected from the group consisting of hydrogen, $C_1$–$C_5$ alkyl, $C_1$–$C_5$ alkoxy, fluoro and chloro, $Z_2$ is selected from the group consisting of $C_1$–$C_5$ alkyl, $C_1$–$C_5$ alkoxy, cyano, hydroxy, halogen, acrylyl, methacrylyl, acryloxy ($C_1$–$C_4$) alkyl and methacryloxy ($C_1$–$C_4$) alkyl, and a is an integer of from 0 to 2, and B' is selected from the group consisting of the unsubstituted or substituted heterocyclic aromatic groups pyridyl, thienyl, benzothienyl, furyl, and benzofuryl, or (ii) B and B' taken together form the adamantyl group, said heterocyclic group substituents being selected from $C_1$–$C_4$ alkyl, $C_1$–$C_4$ haloalkyl, $C_1$–$C_4$ alkoxy, $C_1$–$C_4$ alkoxy ($C_1$–$C_4$)alkyl, di($C_1$–$C_5$)alkylamino, and halogen, said halogen and halo substituents being fluorine, chlorine or bromine.

3. The naphthopyran of claim 2 wherein L is $C_1$–$C_4$ alkyl, $C_6$–$C_7$ aryl($C_1$–$C_2$) alkyl, $C_5$–$C_6$ cycloalkyl, or $C_1$–$C_2$ alkyl substituted $C_5$–$C_6$ cycloalkyl.

4. The naphthopyran of claim 2 wherein $R_8$ is methoxy, chloro or bromo.

5. The naphthopyran of claim 4 wherein $Z_1$ is $C_1$–$C_3$ alkyl, $C_1$–$C_3$ alkoxy or fluoro; $Z_2$ is selected from the group consisting of $C_1$–$C_3$ alkyl and $C_1$–$C_3$ alkoxy; and a is 0 or 1.

6. The naphthopyran of claim 5 wherein the position of $Z_2$ is meta or para to the carbon atom attached to the pyran ring when a is 1.

7. A photochromic article comprising a polymerized organic host material and a photochromic amount of a naphthopyran compound represented by the following graphic formula:

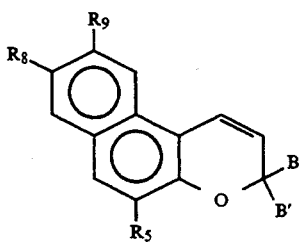

wherein $R_5$ and $R_9$ are each selected from the group consisting of hydrogen, $C_1$–$C_4$ alkoxy and $C_1$–$C_4$ alkyl, $R_8$ is selected from the group consisting of halogen, $C_1$–$C_5$ acyloxy, benzoyloxy, methoxybenzoyloxy, di($C_1$–$C_5$)alkylamino, and LO—, wherein L is a $C_1$–$C_{12}$ alkyl, $C_6$–$C_9$ aryl($C_1$–$C_3$)alkyl, $C_5$–$C_7$ cycloalkyl, or $C_1$–$C_4$ alkyl substituted $C_5$–$C_7$ cycloalkyl, and wherein (i)B is selected from the group consisting of the unsubstituted or substituted phenyl, and B' is selected from the group consisting of the unsubstituted or substituted heterocyclic aromatic groups pyridyl, thienyl, benzothienyl, furyl, and benzofuryl, or (ii) B and B' taken together form the adamantyl group, said aryl and heterocyclic group substituents each being selected from $C_1$–$C_4$ alkyl, $C_1$–$C_4$ haloalkyl, $C_1$–$C_4$ alkoxy, $C_1$–$C_4$ alkoxy($C_1$–$C_4$)alkyl, di($C_1$–$C_5$)alkylamino, and halogen, said halogen and halo substituents being selected from the group consisting of fluorine, chlorine and bromine.

8. The photochromic article of claims 7 wherein the organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonates, polyurethanes, poly(ethylene terephthalate), polystyrene, copoly(styrene-methylmethacrylate), copoly(styrene-acrylonitrile), polyvinylbutyral, and polymers of diallylidene pentaerythritol.

9. A photochromic article comprising a polymerized organic host material and a photochromic amount of a naphthopyran represented by the following graphic formula:

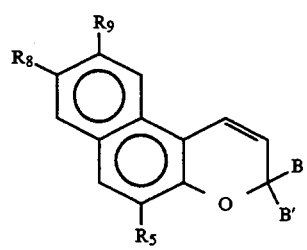

wherein $R_5$ and $R_9$ are each selected from the group consisting of hydrogen, $C_1$–$C_4$ alkoxy and $C_1$–$C_4$ alkyl, $R_8$ is selected from the group consisting of halogen, $C_1$–$C_5$ acyloxy, benzoyloxy, methoxybenzoyloxy, di($C_1$–$C_5$)alkylamino, and LO—, wherein L is a $C_1$–$C_{12}$ alkyl, $C_6$–$C_9$ aryl($C_1$–$C_3$)alkyl, $C_5$–$C_7$ cycloalkyl, or $C_1$–$C_4$ alkyl substituted $C_5$–$C_7$ cycloalkyl, and wherein (i)B is a phenyl group represented by the following graphic formula:

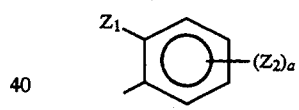

wherein $Z_1$ is selected from the group consisting of hydrogen, $C_1$–$C_5$ alkyl, $C_1$–$C_5$ alkoxy, fluoro and chloro, $Z_2$ is selected from the group consisting of $C_1$–$C_5$ alkyl, $C_1$–$C_5$ alkoxy, cyano, hydroxy, halogen, acrylyl, methacrylyl, acryloxy ($C_1$–$C_4$) alkyl and methacryloxy ($C_1$–$C_4$) alkyl, and a is an integer of from 0 to 2, and B' is selected from the group consisting of the unsubstituted or substituted heterocyclic aromatic groups pyridyl, thienyl, benzothienyl, furyl, and benzofuryl, or (ii) B and B' taken together form the adamantyl group, said heterocyclic group substituents being selected from $C_1$–$C_4$ alkyl, $C_1$–$C_4$ haloalkyl, $C_1$–$C_4$ alkoxy, $C_1$–$C_4$ alkoxy ($C_1$–$C_4$)alkyl, di($C_1$–$C_5$)alkylamino, and halogen, said halogen and halo substituents being fluorine, chlorine or bromine.

10. The photochromic article of claim 9 wherein $R_8$ is $C_1$–$C_4$ alkoxy, chloro or bromo.

11. The photochromic article of claim 10 wherein $R_8$ is methoxy.

12. The photochromic article of claim 10 wherein $Z_1$ is $C_1$–$C_3$ alkyl, $C_1$–$C_3$ alkoxy or fluoro; $Z_2$ is selected from the group consisting of $C_1$–$C_3$ alkyl and $C_1$–$C_3$ alkoxy; and a is 0 or 1.

13. The photochromic article of claim 12 wherein the position of $Z_2$ is meta or para to the carbon atom attached to the pyran ring when a is 1.

14. The photochromic article of claim 12 wherein the organic host material is a solid transparent homopolymer or copolymer of diethylene glycol bis(allyl carbonate), the carbonate-linked resin derived from a bisphenol and phosgene, polymethylmethacrylate, a polyacrylate, a polyurethane or polyvinylbutyral.

15. The photochromic article of claim 14 wherein the photochromic compound is present in an amount of from about 0.01 to 20 weight percent.

16. The photochromic article of claim 37 wherein the article is a lens.

* * * * *